United States Patent [19]
Cassell et al.

[11] Patent Number: 5,827,324
[45] Date of Patent: Oct. 27, 1998

[54] DISTAL PROTECTION DEVICE

[75] Inventors: Robert L. Cassell, Otsego; John M. K. Daniel, Hopkins; Thomas V. Ressemann, St. Cloud, all of Minn.

[73] Assignee: SciMed Life Systems, Inc., Maple Grove, Minn.

[21] Appl. No.: 813,794

[22] Filed: Mar. 6, 1997

[51] Int. Cl.$^6$ .................................................. A61M 29/00
[52] U.S. Cl. ........................ 606/200; 606/194; 606/198; 604/22
[58] Field of Search .................................. 606/159, 180, 606/200, 191, 194, 195, 198; 604/22, 104

[56] References Cited

U.S. PATENT DOCUMENTS

| | | |
|---|---|---|
| 4,425,908 | 1/1984 | Simon . |
| 4,447,227 | 5/1984 | Kotsanis ..................... 604/95 |
| 4,590,938 | 5/1986 | Segura et al. . |
| 4,706,671 | 11/1987 | Weinrib . |
| 4,723,549 | 2/1988 | Wholey et al. . |
| 4,728,319 | 3/1988 | Masch ........................ 604/22 |
| 4,790,812 | 12/1988 | Hawkins, Jr. et al. ............ 604/22 |
| 4,790,813 | 12/1988 | Kensey ....................... 604/22 |
| 4,794,928 | 1/1989 | Kletschka . |
| 4,873,978 | 10/1989 | Ginsburg . |
| 4,926,858 | 5/1990 | Gifford, III et al. ............. 606/159 |
| 4,998,539 | 3/1991 | Delsanti ..................... 128/898 |
| 5,053,008 | 10/1991 | Bajaj ........................ 604/104 |
| 5,071,407 | 12/1991 | Termin et al. ................. 604/104 |
| 5,100,423 | 3/1992 | Fearnot ...................... 606/159 |
| 5,102,415 | 4/1992 | Guenther et al. ............... 606/159 |
| 5,329,942 | 7/1994 | Gunther et al. ................ 128/898 |
| 5,354,310 | 10/1994 | Garnic et al. ................. 606/198 |
| 5,376,100 | 12/1994 | Lefebvre .................... 606/180 |
| 5,421,832 | 6/1995 | Lefebvre .................... 604/53 |
| 5,549,626 | 8/1996 | Miller et al. ................. 606/200 |

FOREIGN PATENT DOCUMENTS

| | | |
|---|---|---|
| 0 737 450 A1 | 10/1996 | European Pat. Off. . |
| 2821048 | 11/1979 | Germany . |
| WO 94/24946 | 11/1994 | WIPO . |
| WO 96/01591 | 1/1996 | WIPO . |

OTHER PUBLICATIONS

*The Journal of Invasive Cardiology,* vol. 8, Supplement E, 1996, "Stents Don't Require Systemic Anticoagulation . . . But the Technique (and Results) Must Be Optimal", by Issaam Moussa, MD, et al., pp. 3E–30E, Health Management Publications, Inc.

*Primary Examiner*—Gary Jackson
*Attorney, Agent, or Firm*—Westman, Champlin & Kelly, P.A.

[57] ABSTRACT

An emboli capturing system captures emboli in blood flowing through vasculature. The emboli capturing system includes a guidewire having a longitudinal axis and defining a lumen. An expandable member is coupled to a distal portion of the guidewire and has an interior which is in fluid communication with the lumen in the guidewire. An emboli capturing device is operably coupled to the expandable member and configured to deploy radially outwardly relative to the guidewire upon expansion of the expandable member.

20 Claims, 3 Drawing Sheets

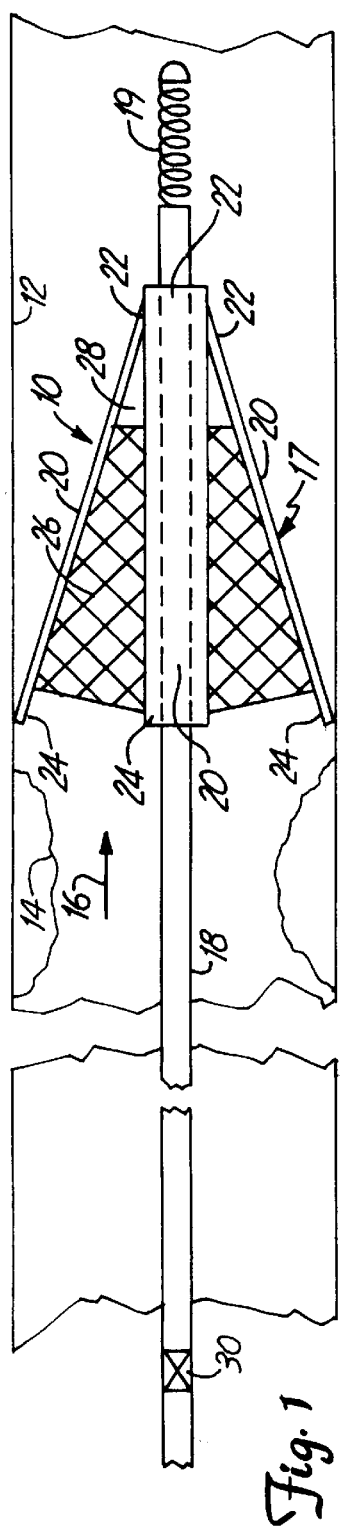
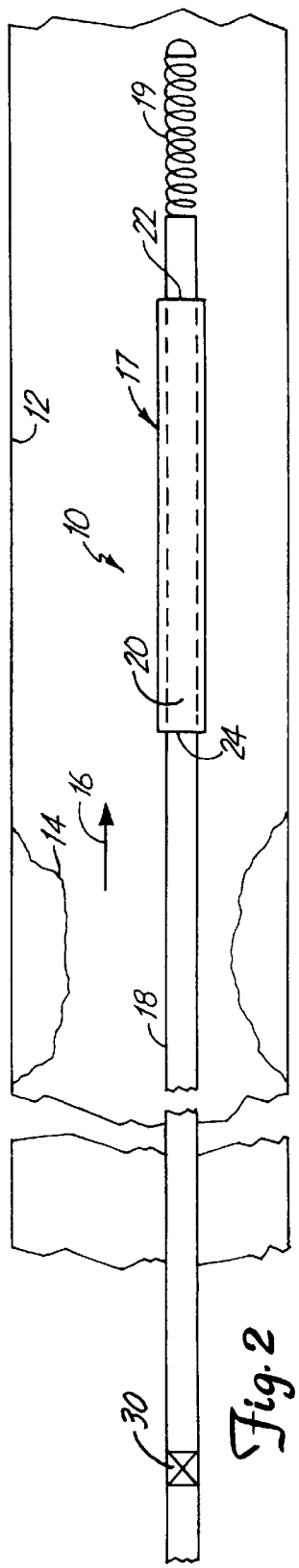
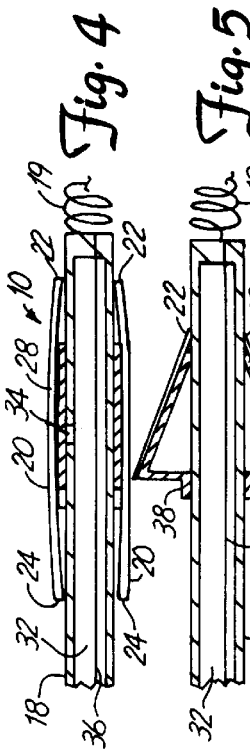
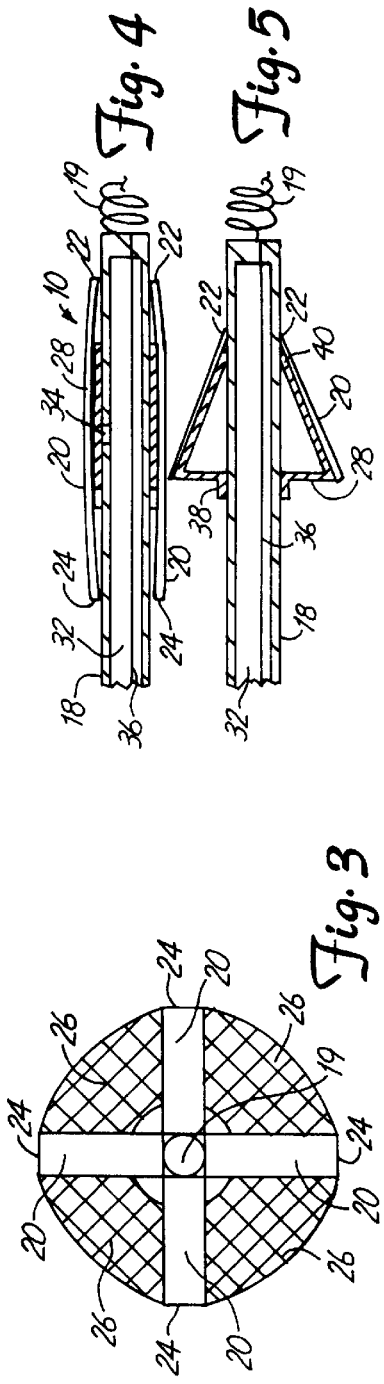

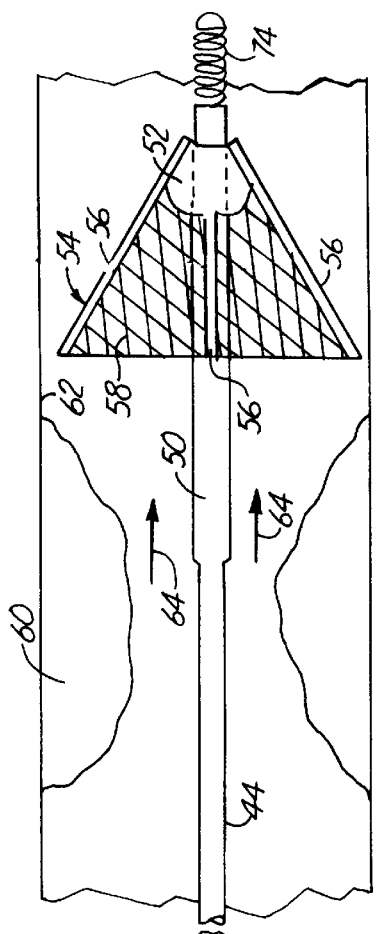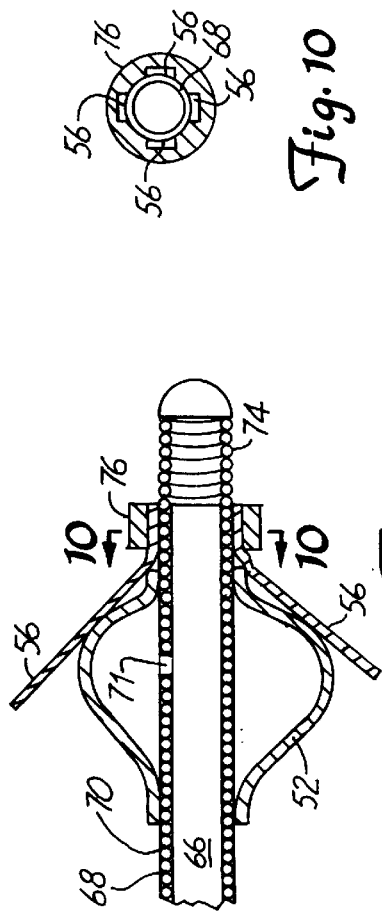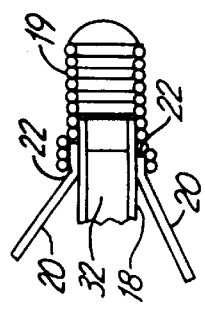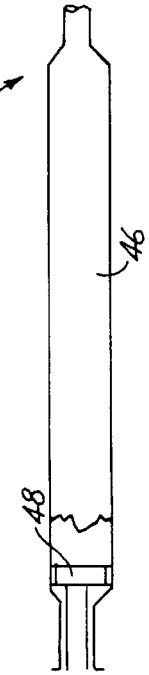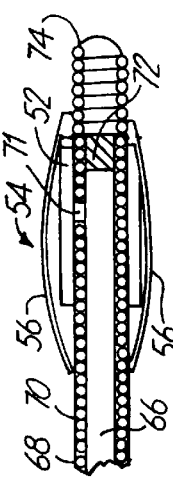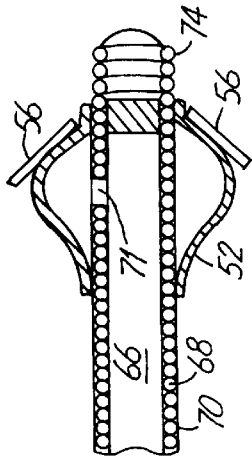

DISTAL PROTECTION DEVICE

BACKGROUND OF THE INVENTION

The present invention deals with an emboli capturing system. More specifically, the present invention deals with an emboli capturing system for capturing embolic material in a blood vessel during an atherectomy, balloon dilatation, stenting or thrombectomy procedure.

Blood vessels can become occluded (blocked) or stenotic (narrowed) in one of a number of ways. For instance, a stenosis may be formed by an atheroma which is typically a harder, calcified substance which forms on the lumen walls of the blood vessel. Also, the stenosis can be formed of a thrombus material which is typically much softer than an atheroma, but can nonetheless cause restricted blood flow in the lumen of the blood vessel. Thrombus formation can be particularly problematic in a saphenous vein graft (SVG).

Two different procedures have developed to treat a stenotic lesion (stenosis) in vasculature. The first is to deform the stenosis to reduce the restriction within the lumen of the blood vessel. This type of deformation (or dilatation) is typically performed using balloon angioplasty.

Another method of treating stenotic vasculature is to attempt to completely remove either the entire stenosis, or enough of the stenosis to relieve the restriction in the blood vessel. Removal of the stenotic lesion has been done through the use of radio frequency (RF) signals transmitted via conductors, and through the use of lasers, both of which treatments are meant to ablate (i.e., super heat and vaporize) the stenosis. Removal of the stenosis has also been accomplished using thrombectomy or atherectomy. During thrombectomy and atherectomy, the stenosis is mechanically cut or abraded away from the vessel.

Certain problems are encountered during thrombectomy and atherectomy. The stenotic debris which is separated from the stenosis is free to flow within the lumen of the vessel. If the debris flows distally, it can occlude distal vasculature and cause significant problems. If it flows proximally, it can enter the circulatory system and form a clot in the neural vasculature, or in the lungs, both of which are highly undesirable.

Prior attempts to deal with the debris or fragments have included cutting the debris into such small pieces (having a size on the order of a blood cell) that they will not occlude vessels within the vasculature. However, this technique has certain problems. For instance, it is difficult to control the size of the fragments of the stenotic lesion which are severed. Therefore, larger fragments can be severed accidentally. Also, since thrombus is much softer than an atheroma, it tends to break up easier when mechanically engaged by a cutting instrument. Therefore, at the moment that the thrombus is mechanically engaged, there is a danger that it can be dislodged in large fragments which would occlude the vasculature.

Another attempt to deal with debris severed from a stenosis is to remove the debris, as it is severed, using suction. However, it may be necessary to pull quite a high vacuum in order to remove all of the pieces severed from the stenosis. If a high enough vacuum is not used, all of the severed pieces will not be removed. Further, when a high vacuum is used, this can tend to cause the vasculature to collapse.

A final technique for dealing with the fragments of the stenosis which are severed during atherectomy is to place a device distal to the stenosis during atherectomy to catch the pieces of the stenosis as they are severed, and to remove those pieces along with the capturing device when the atherectomy procedure is complete. Such capture devices have included expandable filters which are placed distal of the stenosis to capture stenosis fragments. However, such prior devices have typically been supported by over-the-wire devices such as balloon angioplasty catheters. Over-the-wire devices of this type have a fairly large outer diameter which can, under some circumstances, be undesirable.

SUMMARY OF THE INVENTION

A emboli capturing system filters blood flowing through the vasculature. The emboli capturing system includes a guidewire having a longitudinal axis and defining a lumen. An expandable member is coupled to a distal portion of the guidewire and has an interior which is in fluid communication with the lumen in the guidewire. A capturing element is operably coupled to the expandable member and is configured to deploy radially outwardly relative to the guidewire upon expansion of the expandable member.

BRIEF DESCRIPTION OF THE DRAWINGS

FIG. 1 shows a distal protection device of the present invention in a deployed position.

FIG. 2 shows the distal protection device shown in FIG. 1 in a collapsed position.

FIG. 3 shows an end view of the distal protection device shown in FIGS. 1 and 2.

FIGS. 4 and 5 show a cross-sectional view of a portion of the distal protection device shown in FIGS. 1–3 in the collapsed and deployed positions, respectively.

FIGS. 5A and 5B show a cross-sectional view of a portion of a distal protection device illustrating one embodiment of how the capturing element is connected to the guidewire.

FIG. 6 shows a second embodiment of a distal protection device according to the present invention.

FIGS. 7 and 8 show cross-sectional views of a portion of the distal protection device shown in FIG. 6 in the collapsed and deployed positions, respectively.

FIGS. 9 and 10 illustrate a second embodiment of how the capturing element of the present invention is connected to the guidewire.

DETAILED DESCRIPTION OF THE PREFERRED EMBODIMENTS

Figure 11:
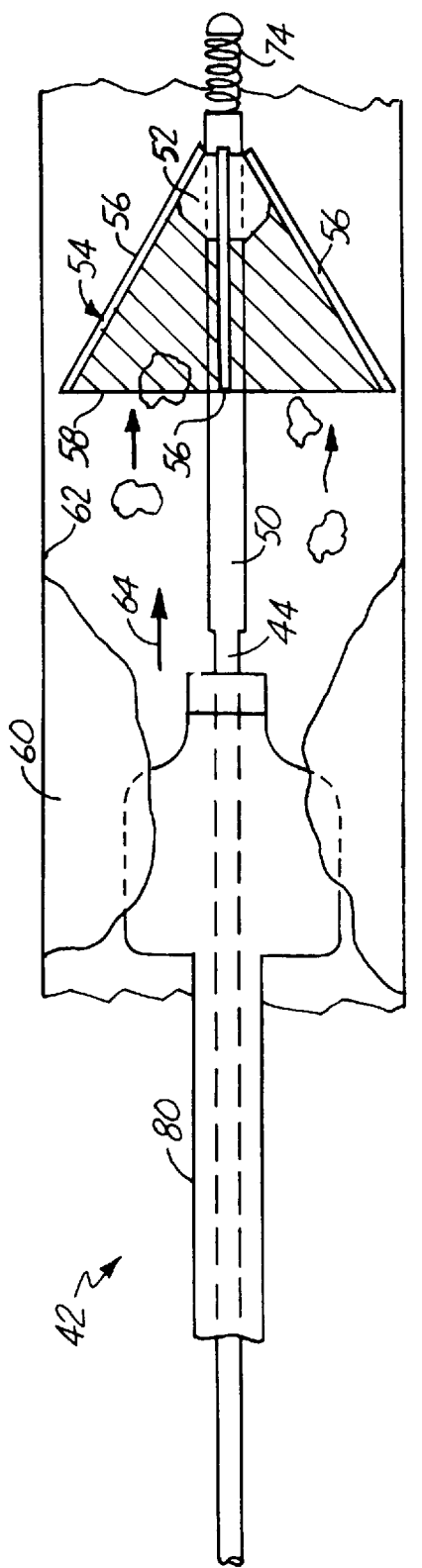
FIG. 11 illustrates a method of using the distal protection device according to the present invention.

FIG. 1 illustrates protection device 10 in a deployed position. Protection device 10 preferably includes hollow guidewire 18 (or a hypotube having the same general dimensions as a guidewire) having a coil tip 19, and a capturing assembly 17 including a plurality of struts or wires 20, mesh 26 and inflatable member 28. The plurality of struts or wires 20 are operably coupled to a distal region of hollow guidewire 18. The connection is preferably a hinge-type connection, so that the struts 20 have distal ends 22 which are coupled closely proximate the outer diameter of hollow guidewire 18 and proximal ends 24. When deployed, proximal ends 24 are pivoted radially away from hollow guidewire 18. Mesh 26 is preferably formed of woven, knitted, or braided fibers or wires or other suitable filtering or netting-type material. Portions of mesh 26 extend between struts 20. Inflatable member 28 is preferably coupled in fluid communication with an inner lumen (shown in FIGS. 4 and 5) which runs longitudinally within hollow guidewire 18.

Hollow guidewire 18 also preferably has a valve 30 coupled in a proximal portion thereof. During operation, a syringe is preferably connected to the proximal end of guidewire 18, which preferably includes a fluid filled hypotube. The syringe is used to pressurize the fluid such that fluid is introduced through the lumen of hollow guidewire 18, through valve 30, and into inflatable member 28. Upon being inflated, inflatable member 28 preferably drives struts 20 to assume a deployed position in which ends 24 are pivotally or otherwise moved radially away from hollow guidewire 18 to a diameter which approximates the inner diameter of lumen 12. In this way, capturing assembly or filter 17 is deployed distally of stenosis 14 so that stenosis 14 can be severed and fragmented, and the fragments from stenosis 14 are carried by blood flow (indicated by arrow 16) into the basket or chamber formed by the deployed filter 17. Filter 17 is then collapsed and removed from vessel 12 with the fragments contained therein.

FIG. 2 illustrates protection device 10 with filter 17 in the collapsed position. Similar items to those shown in FIG. 1 are similarly numbered. FIG. 2 illustrates that mesh 26 is easily collapsible beneath struts 20. In order to collapse filter 17, fluid is preferably removed from inflatable member 28 through the lumen of hollow guidewire 18 and through two-way valve 30. This can be done using the syringe to pull a vacuum or using any other type of suitable fluid removal system.

Struts 20 are preferably formed of a resilient material which has some shape memory. Thus, when inflatable member 28 is collapsed, struts 20 also collapse to approximate the outer diameter of hollow guidewire 18. In another preferred embodiment, struts 20 are fastened to inflatable member 28 through adhesive, or another suitable connector, so that they are effectively pulled to the collapsed position shown in FIG. 2 when the fluid is removed from inflatable member 28. In yet another preferred embodiment, inflatable member 28 is formed of a resilient, shape memory material. In that instance, inflatable member 28 is inflated by introducing fluid under pressure through the lumen in hollow guidewire 18 and into inflatable member 28. When pressure is released from the lumen in hollow guidewire 18, inflatable member 28 is allowed to force fluid out from the interior thereof through two-way valve 30 and to resume its initial collapsed position. Again, this results in filter 17 assuming its collapsed position illustrated by FIG. 2.

FIG. 3 illustrates a view, taken from the distal end of device 10. FIG. 3 shows that, when struts 20 are deployed outwardly, mesh 26 forms a substantially lumen-filling filter which allows blood to flow therethrough, but which provides a mechanism for receiving and retaining stenosis fragments carried into mesh 26 by blood flow through the vessel.

FIG. 4 is a cross-sectional view of a portion of protection device 10. FIG. 4 shows protection device 10 with filter 17 in the collapsed position. FIG. 4 also better illustrates that guidewire 18 is hollow and has a longitudinal lumen 32 running therethrough. Longitudinal lumen 32 is connected in fluid communication with an interior of inflatable member 28 through aperture 34 which is provided in the wall of guidewire 18. FIG. 4 also shows that, in one preferred embodiment, a core wire 36 extends through lumen 32 from a proximal end thereof, where it is brazed to a portion of a hypotube which may be connected to the proximal portion of guidewire 18. The core wire 36 extends to the distal end of guidewire 18 where it is connected to coil tip 19. In one preferred embodiment, coil tip 19 is brazed or otherwise welded or suitably connected to the distal portion of core wire 36.

FIG. 5 shows protection device 10 with inflatable member 28 in the inflated or deployed position. In the preferred embodiment, it can be seen that member 28 has a conical shape when inflated. This can be obtained in any number of ways, including using a material which is preset to maintain this shape upon inflation. FIG. 5 further illustrates that, in the preferred embodiment, inflatable member 28 has a proximal portion 38 which is connected to the exterior surface of guidewire 18. This connection can be made through adhesive or any other suitable connection mechanism. FIG. 5 also shows that member 28 has a distal portion 40 which is also connected about the periphery of guidewire 18. As with the proximal portion 38, distal portion 40 can be connected using any suitable connection mechanism.

FIGS. 5A and 5B illustrate a method of attaching struts 20 to the outer periphery of guidewire 18. FIG. 5A shows that the distal ends 22 of struts 20 are substantially flattened flange portions which lie substantially flat against the external periphery of the distal portion of guidewire 18. In the embodiment shown in FIGS. 5A and 5B, coil 19 is expanded to fit about not only the external periphery of guidewire 18, but also about the distal portions 22 of struts 20. Coil 19 extends beyond the distal end of guidewire 18 to form the spring tip thereof. In addition, it should be noted that coil 19 can be secured to the external periphery of guidewire 18 either by a tight frictional fit, or by a suitable adhesive, brazing, or another suitable form of connection.

FIG. 6 illustrates a second embodiment of a distal protection device 42 in accordance with present invention. Device 42 includes a hollow guidewire 44 which has a lumen extending longitudinally therethrough. Guidewire 44 preferably includes a midshaft portion defining a widened fluid chamber 46. The widened fluid chamber 46 is configured to receive a syringe piston 48 slidably therein. Guidewire 44 also includes a distal end 50 which comprises a coil encapsulated in polymer material. The interior of the encapsulated coil communicates with the lumen in the remainder of guidewire 44. The interior of the coil is also in fluid communication with the interior of an inflatable member 52 coupled to the distal portion of distal end 50. Device 42 also includes a filter 54 which is similar to the filter shown with respect to device 10 in FIG. 1, except that struts 56 are preferably much thinner than struts 20 and are comprised of wires which have a memory. Struts 56 have mesh or netting portions 58 coupled therebetween as with device 10.

In operation, filter 54 is advanced past stenosis 60 in the lumen of blood vessel 62. Advancement of filter 54 is accomplished with filter 54 in the collapsed position (shown in greater detail in FIG. 7). The treating physician then causes piston 48 to move distally within chamber 46. This causes displacement of fluid within chamber 46, and causes that fluid to move through the lumen of guidewire 44 and through the coil at distal end 50 into inflatable member 52. Inflatable member 52 inflates causing struts 56 to deploy radially outwardly and causing filter 54 to assume a substantially conical shape. Filter 54 is then positioned to receive fragments of stenosis 60 which are carried distally by the blood flow in vessel 62, the blood flow being indicated generally by arrows 64.

Once removal of stenosis 60 has been accomplished, the physician withdraws piston 48 proximally within chamber 46. The piston pulls a vacuum which draws fluid from within inflatable member 52 causing it to collapse. This causes filter 54 to collapse and to approximate the outer diameter of the distal portion 50 of guidewire 44. Filter 54 is then removed, carrying with it the fragments which entered filter 54. Since the volume of inflatable member 52 is so small, and since the cross-section of the lumen through guidewire 44 is typically quite small, the fluid used to inflate inflatable member 52 may be either a gas or a suitable liquid.

It should be noted that, as described in greater detail with respect to FIG. 11, the stenosis removal device (or atherectomy catheter) used to fragment stenosis 60 can be advanced over guidewire 44. Thus, the device according to the present invention is dual functioning in that it captures emboli and serves as a guidewire. Therefore, the present invention does not require adding an additional device to the procedure. Instead, the present invention simply replaces a conventional guidewire with a multifunctional device.

FIG. 7 is a cross-sectional view of a portion of device 42 showing filter 54 in the collapsed position. FIG. 7 shows that the interior of inflatable member 52 is in fluid communication, through aperture 71, with the longitudinal lumen 66 in distal end 50 of guidewire 44. FIG. 7 also shows that distal portion 50 is formed of a coil 68 which is encapsulated in a polymer material 70. Coil 68 extends beyond an end member 72 to form coil spring tip 74 on device 42.

FIG. 8 is a cross-sectional view of a portion of filter 54 in the deployed position. Filter 54 operates in a similar fashion to filter 17 shown in FIG. 5, except that inflatable member 52 is shaped more like a diamond or a traditional inflatable balloon.

In the embodiment shown in FIGS. 6–8, the entire distal half of the shaft of guidewire 44 is preferably formed of a polymer material. Distal end 50 is formed of the polymer encased coil which provides flexibility and resilience. A proximal stainless steel hypotube can also be used or the entire shaft can be formed of a suitable polymer material.

FIG. 9 is similar to FIG. 8 except that it shows an alternative system for connecting wire struts 56 to the outside of tube 44. In the embodiment shown in FIG. 9, an annular ring 76 is disposed about the distal ends of struts 56.

FIG. 10 shows a cross-sectional view of a portion of annular ring 76 and struts 56 taken along section lines 10—10 in FIG. 9. FIG. 10 shows that the distal portion of struts 56 are welded within small notches formed in the inner periphery of annular ring 76. During assembly, annular ring 76 is first formed, and then struts 56 are welded therein. This assembly is then preferably slid over the shaft 44 of device 42 and secured in place at the distal end thereof using a suitable adhesive, brazing, or another suitable form of connection.

FIG. 11 illustrates use of a device 10 or 42 according to the present invention. For the sake of clarity, the present description proceeds with respect to device 42 only. Device 42 is shown filtering stenosis fragments from the blood flowing through the lumen of vessel 62. Also shown in FIG. 11 is a dilatation device 80. Device 80 can be any suitable dilatation device for cutting, aspirating, or fragmenting, or abrading, portions of stenosis 60. In the preferred embodiment, device 80 is used in an over-the-wire fashion over guidewire 44. Thus, filter 54 is first advanced (using guidewire 44) distal of stenosis 60. Then, filter 54 is deployed outwardly to the expanded position. Dilatation device 80 is then advanced over guidewire 44 to stenosis 60 and is used to fragment or abrade stenosis 60. The fragments are received within the basket of filter 54. Filter 54 is then collapsed, and filter 54 and dilatation device 80 are removed from vessel 62. Alternatively, dilatation device 80 can be removed first and filter 54 is then removed along with guidewire 44.

Therefore, it can be seen that the present invention provides a filter which can either be biased in the deployed position in which it is expanded radially away from the shaft used to deploy it, or it can be biased in a collapsed position in which it lies against that shaft. In either case, forcing movement of fluid either into or out of the expandable member drives the filter to move between the contracted and expanded positions, or vice versa. By providing such an expandable filter on a guidewire-sized shaft, the present invention provides a number of advantages. First, the present invention can be used with many forms of dilatation devices, while facilitating such use over the guidewire used in actuating the filter. Further, the present invention can be utilized without prior art methods of capturing fragments of stenosis, and without the associated problems.

In one preferred embodiment the struts used in accordance with the present invention were 0.005 inch by 0.020 inch wide and were formed of 304 stainless steel ribbon. Five struts were used approximately 72 degrees from the next about the periphery of the guidewire. The inflatable member was formed using polyethylene terephthalate (PET) and, when inflated, had a diameter of approximately 5 mm and a longitudinal length of approximately 10 mm. In another preferred embodiment, the inflatable member was formed of polyurethane or Teflon filled polyurethane material to create an elastomeric inflatable member.

Further, in the present invention, the preferred guidewire used to deploy the filter has an approximate inside diameter of 0.014 inches and an outside diameter of approximately 0.018 inches. For other coronary applications, different dimensions may also be used, such as outer diameters of approximately 0.010 inches or 0.014 inches.

Further, it will be appreciated that the particular size of the guidewire will vary with application. Applications involving neural vasculature will require the use of a smaller guidewire, while other applications will require the use of a larger guidewire.

Although the present invention has been described with reference to preferred embodiments, workers skilled in the art will recognize that changes may be made in form and detail without departing from the spirit and scope of the invention.

What is claimed is:

1. An emboli capturing system for introduction into vasculature to capture emboli in blood flowing in the vasculature, the emboli capturing system comprising:

a guidewire having a longitudinal axis and defining a lumen along at least a portion thereof;

an expandable member coupled to a distal portion of the guidewire and having an interior being in fluid communication with the lumen in the guidewire, the expandable member being configured to receive fluid through the lumen to expand and have fluid removed from the interior thereof to collapse; and an emboli capturing device operably coupled to the expandable member and configured to deploy radially outwardly relative to the guidewire upon expansion of the expandable member.

2. The emboli capturing system of claim 1 wherein the emboli capturing device comprises a mesh.

3. The emboli capturing system of claim 2 wherein the emboli capturing device comprises:

a plurality of struts operably coupled to the expandable member, each strut having a portion thereof deployed radially outwardly upon expansion of the expandable member, the mesh being coupled to the struts.

4. The emboli capturing system of claim 3 wherein the struts are configured to substantially form a basket having an open end thereof facing proximally, and having a closed end thereof formed about a distal portion of the guidewire.

5. The emboli capturing system of claim 1 wherein the fluid comprises a gas.

6. The emboli capturing system of claim 1 wherein the emboli capturing device is biased in a collapsed position in which it has an outer diameter approximating the outer diameter of the guidewire, and wherein the emboli capturing device is configured such that pressurizing the fluid causes the expandable member to expand and deploy the emboli capturing device radially outwardly relative to the guidewire.

7. The emboli capturing system of claim 1 wherein the emboli capturing device is biased in a deployed position in which it is expanded radially outwardly relative to the guidewire, and wherein removing fluid from the expandable member causes the emboli capturing device to move to a retracted position wherein the emboli capturing device has an outer diameter approximating an outer diameter of the guidewire.

8. The emboli capturing system of claim 3 wherein the struts are coupled to a portion of the guidewire distal to the expandable member and wherein the struts extend proximally over an outer surface of the expandable member.

9. The emboli capturing system of claim 8 wherein the struts are connected between the guidewire and an annular ring.

10. The emboli capturing system of claim 8 wherein the struts are coupled to the guidewire by a coil extending about a portion of the struts and the guidewire.

11. A dilatation system, comprising:
a dilatation device configured to fragment a restriction in a blood vessel; and
an emboli capturing system, longitudinally movable within the blood vessel relative to the dilatation device, the emboli capturing system comprising:
a guidewire having a longitudinal axis and defining a lumen along at least a portion thereof;
an expandable member coupled to a distal portion of the guidewire and having an interior being in fluid communication with the lumen in the guidewire, the expandable member being configured to receive fluid through the lumen to expand and have fluid removed from the interior thereof to collapse; and
an emboli capturing device operably coupled to the expandable member and configured to deploy radially outwardly relative to the guidewire upon expansion of the expandable member.

12. The dilatation system of claim 11 wherein the dilatation device includes a guidewire receiving passageway suitable for tracking over the guidewire.

13. The dilatation system of claim 11 wherein the emboli capturing device comprises a mesh.

14. The dilatation system of claim 13 wherein the emboli capturing device comprises:

a plurality of struts operably coupled to the expandable member, each strut having a portion thereof deployed radially outwardly upon expansion of the expandable member, the mesh being coupled to the struts.

15. The dilatation system of claim 14 wherein the struts are configured to substantially form a conical basket having an open end thereof facing proximally, and having a closed end thereof formed about a distal portion of the guidewire.

16. The dilatation system of claim 11 wherein the emboli capturing device is biased in a collapsed position in which it has an outer diameter approximating the outer diameter of the guidewire, and wherein the emboli capturing device is configured such that pressurizing the fluid causes the expandable member to expand and deploy the emboli capturing device radially outwardly relative to the guidewire.

17. The dilatation system of claim 11 wherein the emboli capturing device is biased in a deployed position in which it is expanded radially outwardly relative to the guidewire, and wherein removing fluid from the expandable member causes the emboli capturing device to move to a retracted position wherein the emboli capturing device has an outer diameter approximating an outer diameter of the guidewire.

18. The dilatation system of claim 14 wherein the struts are coupled to a portion of the guidewire distal to the expandable member and wherein the struts extend proximally over an outer surface of the expandable member.

19. A method of removing a restriction in a blood vessel comprising:
providing a guidewire defining a lumen longitudinally therethrough with an inflatable member coupled to a distal portion of the guidewire and having an interior thereof in fluid communication with the lumen;
providing an emboli capturing device, operably coupled to the expandable member to deploy radially outwardly relative to the guidewire when the expandable member is inflated, and to retract to a retracted position approximating the outer diameter of the guidewire;
inserting the emboli capturing device in the blood vessel;
advancing the emboli capturing device using the guidewire distally of the restriction;
advancing, over the guidewire, a dilatation device;
expanding the expandable member to deploy the emboli capturing device in an expanded position;
fragmenting at least a portion of the restriction using the dilatation device; and
capturing the fragmented portions of the restriction from blood in the blood vessel using the emboli capturing device.

20. The method of claim 19 and further comprising:
moving the emboli capturing device to the retracted position retaining the fragments therein; and
removing the emboli capturing device from the blood vessel.

* * * * *